United States Patent [19]

Norrish et al.

[11] Patent Number: 4,804,850
[45] Date of Patent: Feb. 14, 1989

[54] MEASUREMENT OF FLUORESCENCE

[75] Inventors: Richard J. Norrish, Port Willunga; Joseph T. Wiskich, Kensington Park, both of Australia

[73] Assignee: Luminis Pty. Limited, Adelaide, Australia

[21] Appl. No.: 25,733

[22] Filed: Mar. 13, 1987

[30] Foreign Application Priority Data

Mar. 14, 1986 [AU] Australia .............................. PH5040

[51] Int. Cl.[4] ................................................ F21V 9/16
[52] U.S. Cl. .................................. 250/459.1; 356/317; 356/417
[58] Field of Search .......................... 250/458.1, 459.1; 356/317, 318, 417, 418

[56] References Cited

U.S. PATENT DOCUMENTS 3,598,994 8/1971 Markle .................. 356/317
4,084,905 4/1978 Schreiber et al. ................. 250/458.1
4,500,641 2/1985 Vanden Engh et al. ........... 356/318
4,699,510 10/1987 Alguard .............................. 356/417

FOREIGN PATENT DOCUMENTS 2023076 12/1976 Australia .
4607179 10/1979 Australia .
8604988 8/1986 World Int. Prop. O. .......... 356/417

Primary Examiner—Janice A. Howell
Attorney, Agent, or Firm—Wegner & Bretschneider

[57] ABSTRACT

A fluorometer probe head and a method of operating a probe to overcome problems of reflectance.

A preferred embodiment for determination of chlorophyll in plant leaves uses a red LED and a green LED consecutively directed to a particular target spot and a photodiode records fluoresced and reflected signals to provide an accurate result.

12 Claims, 6 Drawing Sheets

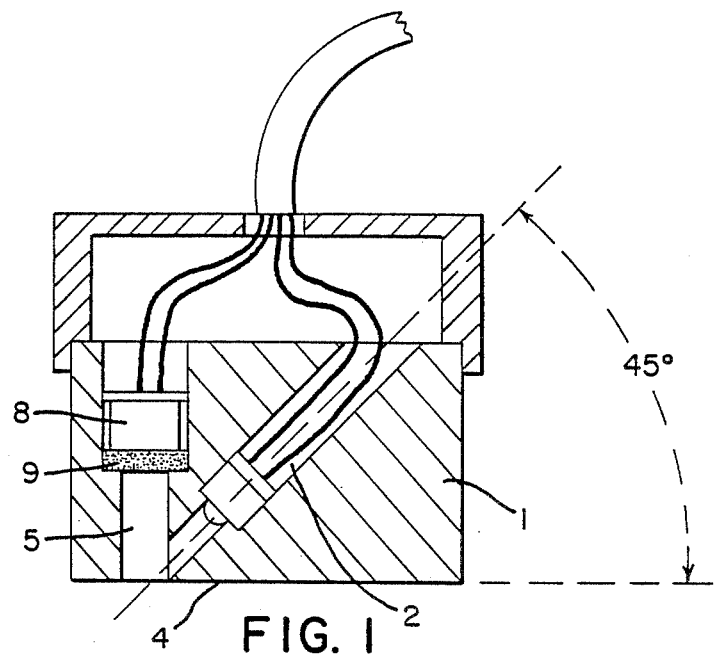
FIG. I
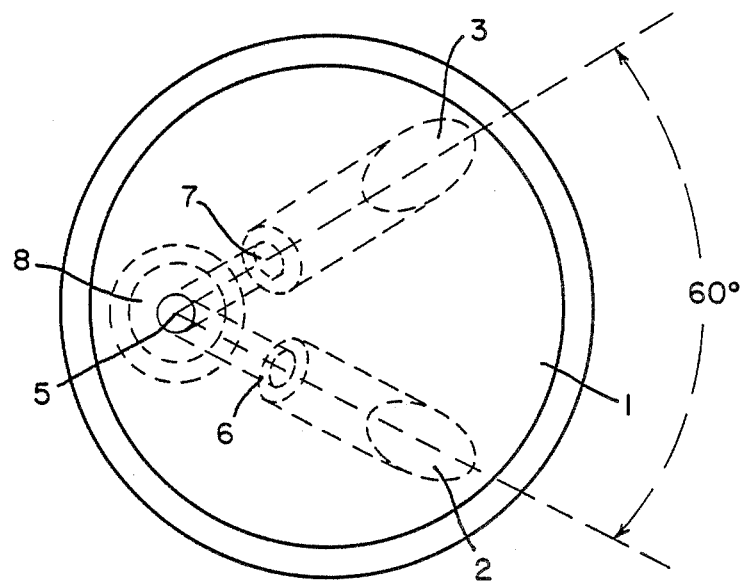
FIG. 2

MEASUREMENT OF FLUORESCENCE

This invention relates to improvements in the measurement of fluorescence and particularly is related to nondestructive testing of fluorescence and to measurement of transient fluorescence.

The measurements of fluorescence of a sample test piece after radiation with electromagnetic radiation of a known frequency or wavelength, can give a qualitative and quantitative measure of the materials present in the test samples.

Problems exist, however, in that if one irradiates the surface of a test sample, then a certain amount of reflectance will occur, and in some situations this reflectance may interfere with the fluorescence signal.

The basic process of fluorescence measurement is to excite the atoms of a test sample with irradiation at one frequency or wavelength, and then to measure the emitted radiation which generally occurs at a slightly different frequency or wavelength. For instance, it is an advantage to know the amount of chlorophyll in leaves to determine how healthy a plant is, and this can be measured by irradiating at a frequency or wavelength which excites atoms of chlorophyll in the leaf which then reradiates at a slightly lower frequency or higher wavelength. The difference in frequencies is not great, however, and a reflected signal can cause a considerable problem in test equipment.

It is the object, therefore, of this invention to provide a fluorescence measuring device which can overcome at least some of the above problems.

In one form, therefore, the invention is said to reside in a method of determining the fluorescence of a test sample at a test point, comprising the steps of determining the gross reflectance and fluorescence of the sample at the test point when excited by electromagnetic radiation at a known first wavelength which causes at least fluorescence in the sample, determining the reflectance of the sample at that test point by radiating the surface with a known but different from the first wavelength electromagnetic radiation at a second wavelength which does not cause fluorescence in the sample and subtracting the reflectance measurement from the gross reflectance and fluorescence value to give a pure fluorescence measurement at the test point.

In one preferred form of the invention the method may use two different emitters and a single collector.

The testing may be done concurrently with the collector being able to separate the signals at two different frequencies, or may be done consecutively such that first the device measures the reflectance and then, a very short time later, the device measures the gross fluorescence and reflectance.

With suitable data processing a device such as this may be used to measure instantaneous fluorescence as well as the changes of fluorescence with time, by the taking of samples at regular periods during irradiation.

It will be noted that this process is a nondestructive testing and hence may be used in the field to measure the fluorescence and hence chlorophyll content of leaves on growing plants.

It must be remembered, however, that this invention is not limited to its application to measurement of fluorescence in plants, and maybe applied to any similar situation where reflectance may interfere with a fluorescence measurement. Such instances may include determination of impurities in metal samples and other forms of chemical or biochemical analyses.

In another form the invention may be said to reside in a detector head for fluorescence measuring devces comprising a pair of electromagnetic radiation emitters, positioned so as to provide respective emitted signals to a surface to be tested and at least one detector to receive reflected and fluoresced signals from the respective emitters, one of the emitters being adapted to transmit at a different frequency or wavelength from the other of said emitters.

In an alternative form of this form of the invention, there may be two emitters but there may be only one detector adapted for broad band reception which may use a wave pass filter to ensure that only radiation at a desired frequency is detected and measured.

One of the electromagnetic radiation emitter may be used for the reflectance measurement and the other emitter used for the gross fluorescence plus reflectance measurement, with suitable data processing circuitry to subtract one measurement from the other to give a pure fluorescence signal.

In one preferred form of the invention, the electromagnetic radiation detectors, when the device is used for measuring chlorophyll fluorescence in leaves, may comprise light emitting diodes with a green light being used to measure the reflectance of the surface of the sample, and a red light being used as the exciting radiation for fluorescence of chlorophyll in the leaf.

In one preferred form of the invention the collector may have a fluorescence sensitivity of electromagnetic having a wavelength radiation between 750 nm to 1050 nm with the red light emitting diode having a bandwidth of 655 nm to 677 nm and the green light emitting diode having a bandwidth of from 556 nm to 580 nm.

The red LED is the emitter which actually causes the fluorescence but this light also includes a proportion of infared which is the same frequency of wavelength range as the desired fluorescence. Hence a green LED is used which is not absorbed by the chlorophyll but includes substantially the same infrared as the LED and which is reflected from the sample and therefore can be subtracted from the signal from the red LED to give a pure fluorescence value.

In actual fact it is preferable to determine the reflectance first and deduct this from subsequently determined gross reflectance and fluorescence signals.

Suitable powers for irradiation may be 200 microeinsteins per square meter per second.

As discussed above the device according to this invention may be used for measuring transient responses as well as instantaneous responses and hence the sample may be irradiated for a very short period of time or may be irradiated continuously and then the fluorescence may be sampled at sample times of 200, 300, 400, 500, 600, 700, 800, 900, 1000, 2000, 3000, 4000, 5000, and 6000 milliseconds.

This then generally describes the invention but to more clearly assist with understanding of the invention, reference will now be made to the accompanying drawings which show a preferred embodiment of the invention.

In the drawings, FIG. 1 shows a general view of a detector head of a plant diagnostic fluorometer probe.

FIG. 2 shows a view of the detector head from the sample side.

Figure 3:
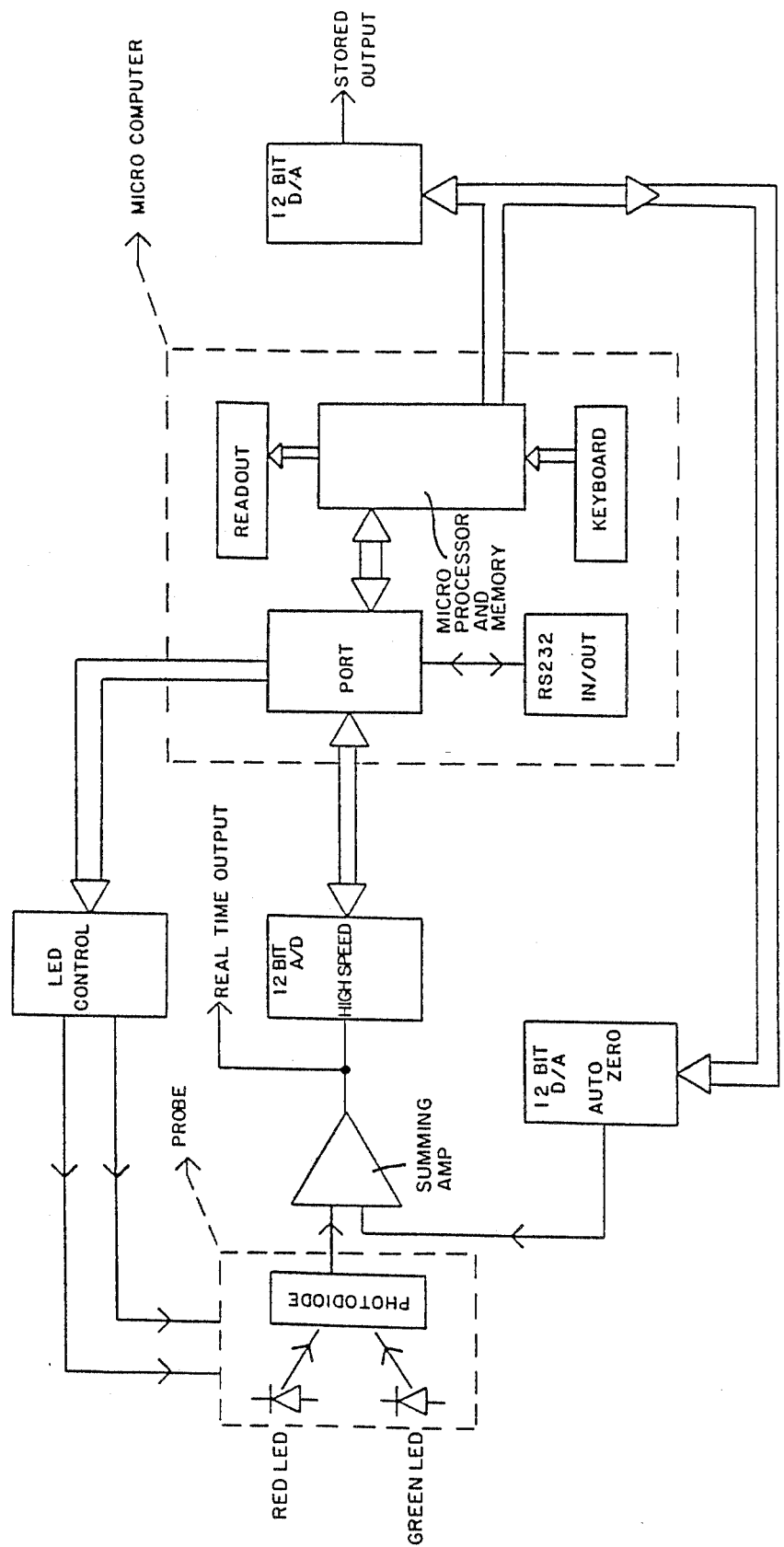
FIG. 3 shows a block diagram of the fluorometer probe.

Now looking more closely at the drawings, and particularly to FIGS. 1 and 2, it will be seen that in this embodiment the detector head comprises a solid block 1, having bored therein angled apertures 2 and 3 which meet at the lower surface 4 of the block 1, and at the same point on surface 4 a vertical drilling 5 is positioned.

In the angled aperture or drilling 2 a red light emitting diode (LED) 6 is positioned and the angled aperture 3 a green light emitting diode (LED) 7 is positioned. A photodiode 8 is mounted in the vertical drilling 5 and a long wavepass filter 9, in this case allowing wavelengths of greater than 750 nanometers to pass, is positioned between the photodiode 8 and the sample surface.

In one preferred embodiment the drillings 2 and 3 are at an angle to each other of 60° measured in the plane of surface 4 and at an angle of 45° to the surface 4 in a vertical plane.

As can be seen in FIG. 3, the probe 10 includes the red LED 6, green LED 7 and photodiode 8. The signal from the photodiode is fed into a summing operational amplifier 11 to sum this with an automatic zero figure provided by block 12 and from this a real time output 13 is provided, or an analogue to digital converter 14 provides a signal to a micro computer 15.

The micro computer 15 provides light emitting diode control 16 and a digital readout 17. Analogue data may be sent to a chart recorder from the digital to analogue converter 18.

The micro computer 15 provides a figure of the fluorescence of a sample by deducting from the gross fluorescence and reflectance signal found when the red LED 6 is actuated the reflectance signal found by use of the green LED 7. The LEDs 6, 7, may be controlled to provide a excitation of a sample and then the input of the photodiode sampled at intervals during the excitation to determine the rae of decay of fluorescence caused by dynamic chemical changes in the leaf.

By the use of the equipment of the present invention resolution of the fluorescence to "time zero" ($F_o$) may be calculated. That is, an instantaneous fluorescence can be experimentally determined by the removal of the errors due to reflection parameters which would cause false "zero" values.

FIGS. 4 to 7 show examples of tests carried out on various leaves and fast transient and slow transient responses to irradiation by red light as discussed above.

Figure 4:
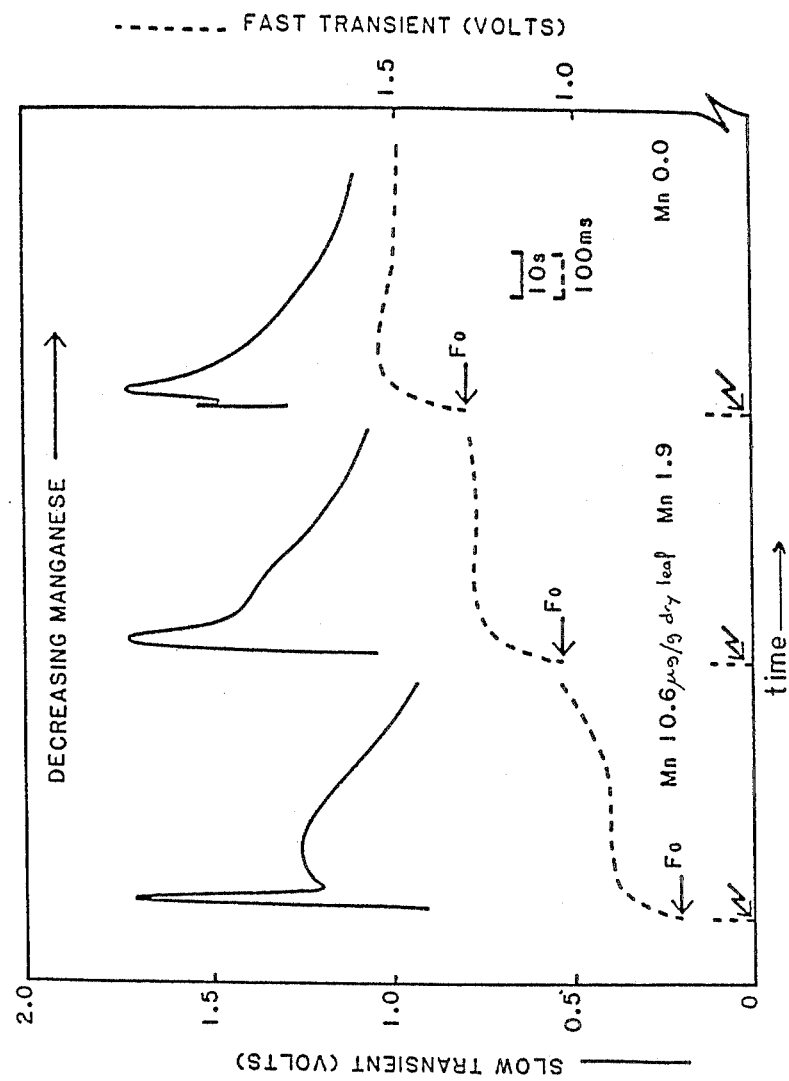
FIGS. 4 to 7 show graphically, test results for measurement of fluorescence of leaves.

FIG. 4 shows the response of wheat leaves containing different amounts of manganese. The solid shows fluorescence patterns in real time taken directly onto a chart recorder over about 50 seconds. The dotted line shows fast transient response of fluorescence over a period of 500 milliseconds. This data is captured by the microcomputer for later display. This enables the value of initial fluorescence ($F_o$) which value is compared to the peak fluorescence $F_p$ as shown by the solid line is the main diagnostic characteristic of manganese deficiency problems.

Figure 5:
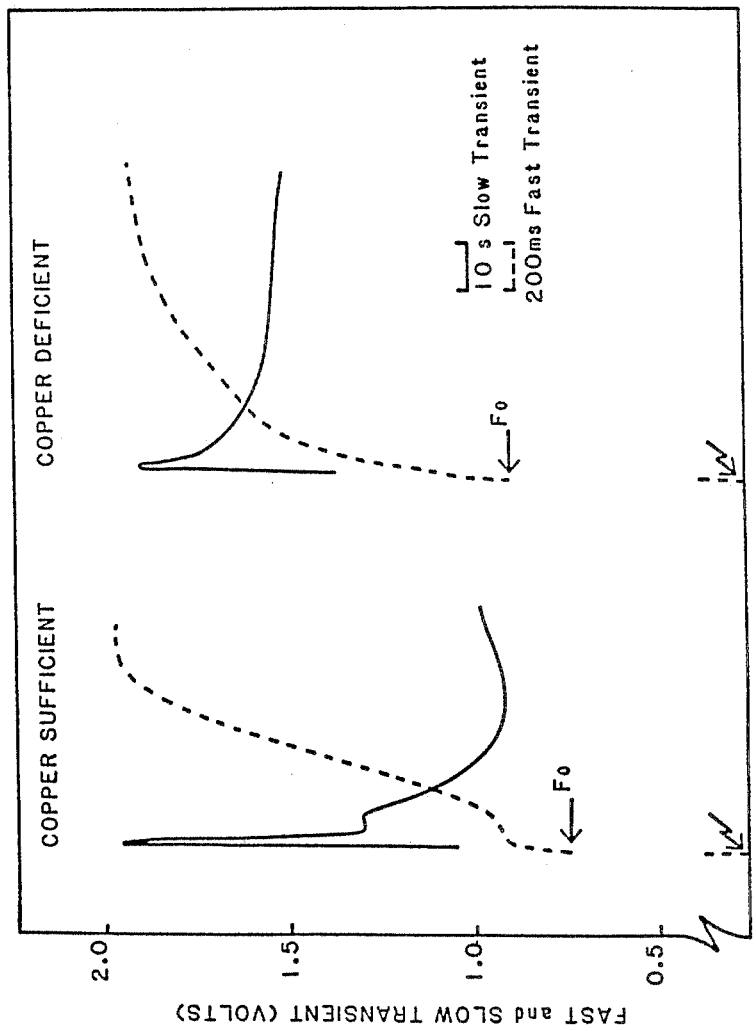

FIG. 5 shows the effect of copper deficiency in wheat leaves with similar characteristics shown in the display as those shown in FIG. 4.

Figure 6:
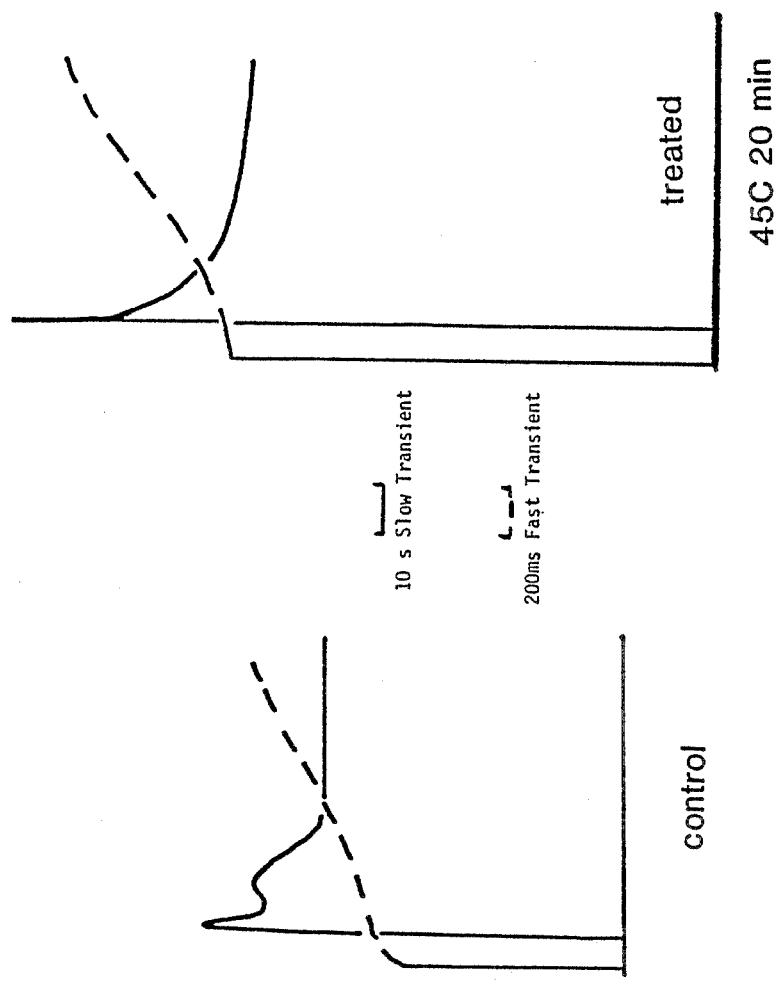

FIG. 6 shows the effect of stress on a plant by determining the fluorescence of chlorophyll in leaves. Leaves of the plant Myall phylloides were heated to 45° C. for 20 minutes to see what difference occured to the initial fluorescence $F_o$.

Figure 7:
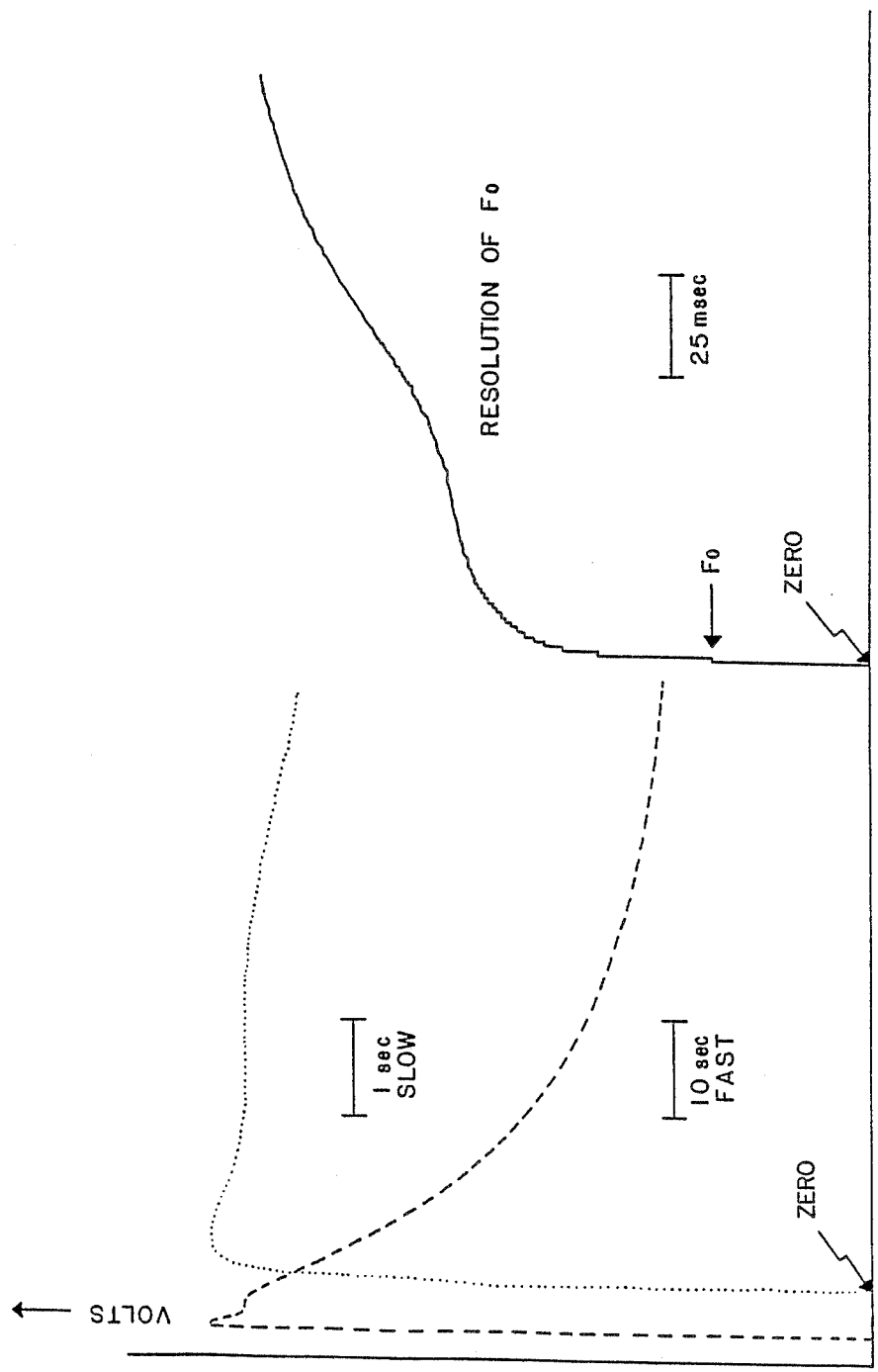

FIG. 7 shows in more detail the type of data capture which may be obtained with the method and apparatus of the present invention. The dashed line shows the fluorescence in real time as traced out on a chart recorder over a period of about one minute. The dotted line shows an expansion of about the first ten seconds of the real time trace and as can be seen very little resolution of the initial fluorescence can be obtained. The solid line shows the effect of the microcomputer stretching the first about 150 milliseconds of the captured fluorescence and this clearly shows the initial jump in the fluorescence after irradiation which is termed $F_o$. It is this value of $F_o$ which is used in plant nutrient deficiency and stress determinations and is so difficult to determine if reflectance problems occur.

This then generally describes the present invention, but it is to be realised, as discussed above, the invention is not limited to measurement of fluorescence in leaves, but may relate to many other materials as well.

The claims defining the invention are as follows.

We claim:

1. A method of determining the instantaneous or transient fluorescence of a test sample at a test point, comprising the steps of
   (a) determining the gross reflectance and fluorescence value of a sample at a test point when excited by light from a first light emitting diode at a first known wavelength which causes at least fluorescence in the sample,
   (b) determining the reflectance at the test point by irradiating the sample with light from a second light emitting diode at a second wavelength which is known but different from the first wavelength and which does not cause fluorescence in the sample and
   (c) subtracting the reflectance from the gross reflectance and fluorescence value to give the fluorescence at the test point,
   wherein a single detector is used to make the determinations of steps (a) and (b).

2. A method as in claim 1 wherein the irradiation with the first and second wavelengths is done consecutively.

3. A method as in claim 1 wherein the first wavelength is in the range of 655 nm to 677 nm and is supplied by a red light emitting diode.

4. A method as in claim 1 wherein the second wavelength is in the range of 556 to 580 nm and is supplied by a green light emitting diode.

5. A method as in claim 1 wherein the detector has a fluorescence sensitivity of electromagnetic radiation having wavelengths of from 750 nm to 1050 nm.

6. A method as in claim 1 wherein the irradiation is at a power of up to 200 microeinsteins per square meter per second.

7. A method as in claim 1 wherein instantaneous fluorescence and decay of fluorescence is determined by carrying out detections at sample times of 200, 300, 400, 500, 600, 700, 800, 900, 1000, 2000, 3000, 4000, 5000 and 6000 milliseconds during the irradiation.

8. A detector head for a device for measuring instantaneous or transient fluorescence, comprising a pair of light emitting diodes, the first of which is a red LED having a bandwidth of 655 to 677 nm and the second of which is a green LED having a bandwidth of 556 to 580 nm, positioned to provide respective emitted signals to a test point on a surface to be tested, and one detector positioned to receive reflected and fluoresced signals from the diodes from the test point.

9. A detector head as in claim 8 wherein a wave pass filter is operatively positioned in front of the detector.

10. A detector head as in claim 8 wherein the detector has a fluorescence sensitivity of electromagnetic radiation having wavelengths of from 750 to 1050 nm.

11. A detector head as in claim 8 wherein the diodes operate at a power of 200 microeinsteins per square meter per second.

12. A detector head as in claim 8, wherein the detector is a photodiode.

* * * * *